(12) United States Patent
Zominy et al.

(10) Patent No.: US 12,133,554 B2
(45) Date of Patent: Nov. 5, 2024

(54) LIQUID DETECTING METHOD AND SYSTEM, AND CARTRIDGE THEREWITH, FOR AN ELECTRONIC CIGARETTE

(71) Applicant: JT International S.A., Geneva (CH)

(72) Inventors: Claude Zominy, Copponex (FR); Oleksiy Didkovskiy, Lviv (UA)

(73) Assignee: JT International S.A. (CH)

( * ) Notice: Subject to any disclaimer, the term of this patent is extended or adjusted under 35 U.S.C. 154(b) by 459 days.

(21) Appl. No.: 17/428,393

(22) PCT Filed: Mar. 5, 2020

(86) PCT No.: PCT/EP2020/055936
§ 371 (c)(1),
(2) Date: Aug. 4, 2021

(87) PCT Pub. No.: WO2020/182632
PCT Pub. Date: Sep. 17, 2020

(65) Prior Publication Data
US 2022/0117313 A1    Apr. 21, 2022

(30) Foreign Application Priority Data
Mar. 12, 2019 (EP) .................................... 19162366

(51) Int. Cl.
*A24F 40/42* (2020.01)
*A24F 40/51* (2020.01)
(Continued)

(52) U.S. Cl.
CPC .............. *A24F 40/42* (2020.01); *A24F 40/51* (2020.01); *G01F 23/00* (2013.01); *G01F 23/292* (2013.01);
(Continued)

(58) Field of Classification Search
CPC .......... A24F 40/10; A24F 40/60; A24F 40/50; A24F 40/40; A24F 40/42; A24F 40/51;
(Continued)

(56) References Cited

U.S. PATENT DOCUMENTS 4,311,048 A * 1/1982 Merz .................... G01F 23/2928
116/227
4,711,126 A * 12/1987 Houpt .................... G01F 23/292
250/577

(Continued)

FOREIGN PATENT DOCUMENTS

| EP | 0450174 A1 * | 10/1991 | |
| GB | 2533652 A * | 6/2016 | ........... A24B 15/167 |
| GB | 2533653 A * | 6/2016 | ............. A24F 40/51 |

OTHER PUBLICATIONS

International Search Report for Application No. PCT/EP2020/055936 mailed Jun. 2, 2020, pp. 1-4.

*Primary Examiner* — Michael P Stafira
(74) *Attorney, Agent, or Firm* — Lerner David LLP

(57) ABSTRACT

A liquid detecting system for an electronic cigarette includes a light source; a light detector; a liquid store including an internal cavity for holding liquid; and a light guide optically coupled to the light source and detector such that light emitted from the source propagates towards the detector along an optical path including an internal reflection within the light guide at a boundary with the cavity, such that light received by the detector along the optical path varies depending on contents of the cavity. Also provided are a liquid cartridge and an electronic cigarette including the system, a method for determining contents of the liquid cartridge and a computer readable medium including executable instructions which, upon execution by a device, cause the method to be performed.

12 Claims, 8 Drawing Sheets

(51) Int. Cl.
*G01F 23/00* (2022.01)
*G01F 23/292* (2006.01)
*G01N 21/17* (2006.01)
*A24F 40/10* (2020.01)

(52) U.S. Cl.
CPC ......... *G01F 23/2928* (2013.01); *G01N 21/17* (2013.01); *A24F 40/10* (2020.01); *A61M 2205/3306* (2013.01)

(58) Field of Classification Search
CPC .......... A24F 40/46; A24F 7/00; A24F 40/485; A24F 40/53; A24F 47/00; A24F 40/90; A24F 40/44; A24F 40/48; A24F 40/20; A24F 40/00; A24F 40/95; A24F 40/65; A24F 13/14; A24F 2700/08; A24F 40/30; A24F 40/57; A24F 7/02; A24F 13/12; A24F 15/015; A24F 1/14; A24F 1/30; A24F 13/04; A24F 40/465; A24F 40/70; A24F 13/00; A24F 13/06; G02B 6/0083; G02B 6/0036; G02B 6/0051; G02B 6/0068; G02B 6/0001; G02B 6/009; G02B 5/003; G02B 6/4201; G02B 6/4298; G02B 6/0005; G02B 6/0006; G02B 6/001; G02B 6/0011; G02B 6/0065; G01N 21/53; G01N 2201/062; G01N 9/00; G01N 21/17; G01N 2021/4166; G01N 21/31; G01F 23/00; G01F 23/292; G01F 23/2928; G01F 1/6888; G01F 1/696; A24D 1/14; A24D 1/002; A24D 1/20; A24D 1/02; A24D 3/17; A24D 1/04

See application file for complete search history.

(56) References Cited

U.S. PATENT DOCUMENTS

| | | | |
|---|---|---|---|
| 10,222,251 B2 * | 3/2019 | Kopansky | G01F 23/292 |
| 2016/0345628 A1 | 12/2016 | Sabet | |
| 2017/0340009 A1 * | 11/2017 | Hon | A24B 15/167 |
| 2018/0020725 A1 * | 1/2018 | Alarcon | A24F 40/40 |
| 2018/0098574 A1 | 4/2018 | Sur et al. | |
| 2018/0220707 A1 * | 8/2018 | Biel | A24F 40/40 |
| 2018/0325183 A1 * | 11/2018 | Huang | G01N 33/0036 |
| 2018/0360119 A1 * | 12/2018 | Kuwa | A24F 40/60 |

* cited by examiner

LIQUID DETECTING METHOD AND SYSTEM, AND CARTRIDGE THEREWITH, FOR AN ELECTRONIC CIGARETTE

CROSS-REFERENCE TO RELATED APPLICATIONS

The present application is a national phase entry under 35 U.S.C. § 371 of International Application No. PCT/EP2020/055936, filed Mar. 5, 2020, published in English, which claims priority to European Application No. 19162366.9 filed Mar. 12, 2019, the disclosures of which are incorporated herein by reference.

FIELD

The present disclosure relates to personal vaporizing devices, such as electronic cigarettes. In particular, aspects of the disclosure relate to a liquid detecting method and system, an electronic cigarette and disposable liquid capsules/cartridges therefor.

BACKGROUND

Electronic cigarettes are an alternative to traditional smoking articles such as cigarettes and cigars. Instead of generating a combustion smoke, they vaporize a liquid, which can be inhaled by a user. The liquid typically comprises an aerosol-forming substance, such as glycerin or propylene glycol that creates the vapor. Other common substances in the liquid are nicotine and various flavorings.

Electronic cigarettes generally comprise a mouthpiece section, a liquid store and a power supply unit. Vaporization is achieved by a vaporizer or heater unit which typically comprises a heating element in the form of a heating coil and a fluid transfer element, such as a wick. The vaporization occurs by the heater heating up the liquid in the fluid transfer element until the liquid is transformed into vapor. The electronic cigarette may be configured to receive disposable consumables in the form of capsules or cartridges. (Capsules comprising the liquid store and the vaporizer are often referred to as "cartridges".) Alternatively, the entire electronic cigarette could be disposable.

An electronic cigarette cannot function without liquid being available to the vaporizer. Further, heating a dry fluid transfer element can lead to an unsatisfactory taste of the vapour, which needs to be avoided. Therefore there is a requirement to determine the liquid level remaining in an electronic cigarette or cartridge. This allows a user to be alerted that the liquid needs to be replenished, for example by replacing a near-empty cartridge or, if the electronic cigarette is single use, that it should be disposed of.

In addition, some types of multi-use electronic cigarettes are configured to operate safely only with certain approved liquids. There is therefore a further requirement to validate that any liquid present is approved for use with that electronic cigarette.

Some means of determining the contents of an electronic cigarette liquid store are described for example in US 2017/0340009 A1, US 2018/0098574 A1 and US 2016/0345628 A1.

Proposed herein are alternative means for determining the contents of an electronic cigarette liquid store for liquid level measurement and/or validation.

SUMMARY

According to a first aspect, there is provided a liquid detecting system (100) for an electronic cigarette (2000), the system comprising: a light source (110, 3110); a light detector (120, 3120); a liquid store (130, 3130, 4130) comprising an internal cavity (131, 3131, 4131) for holding liquid; and a light guide (140, 3140, 4140) optically coupled to both the light source and the light detector such that light emitted from the light source propagates towards the light detector along an optical path comprising an internal reflection within the light guide at a boundary (B) with the cavity, such that light received by the light detector along said optical path varies depending on contents of the cavity.

The light source can for example be a light emitting diode (LED), such as a white LED or a yellow LED, or a laser. The light detector can for example be a photodiode or a charge-coupled device (CCD).

The cavity can comprise liquid having a refractive index, $n_l(f)$, which is higher than the refractive index, $n_g(f)$, of the light guide over at least a portion of a frequency, f, range which the light source is configured to emit and the light detector is configured to detect.

The refractive index, $n_g(f)$, of the light guide can be higher than the refractive index of air over at least a portion of a frequency, f, range which the light source is configured to emit and the light detector is configured to detect.

The frequency, f, range over which the light source is configured to emit and the light detector is configured to detect can for example correspond to a wavelength range of 300 nm to 1500 nm, e.g. 850 nm to 1300 nm.

The refractive index, $n_g(f)$, of the light guide can for example be between 1.45 and 1.50 as conventionally measured at the yellow doublet D-line of sodium, with a wavelength of 589 nm. The light guide can for example be formed of a transparent or translucent material, for example glass or a plastic such as polycarbonate. It could for example be polyethylene, which has a refractive index of 1.458 or poly(methyl methacrylate) (PMMA), which has a refractive index of 1.4906. Any surfaces of the light guide contacting the liquid should be formed of food grade approved substances so as not to contaminate the liquid. The light guide could be solid, or could for example be a liquid or gas-filled tube. In the latter case, the thickness of the tube walls and the liquid or gas filling it can be chosen to provide a suitable refractive index.

The refractive index, $n_l(f)$ of the liquid can for example be between 1.40 and 1.50 as conventionally measured at the yellow doublet D-line of sodium, with a wavelength of 589 nm. For example, it may be propylene glycol (PG), which has a refractive index of 1.4399, or vegetable glycerine (VG), which has a refractive index of 1.4731, or a mixture of these.

The light source can be located with respect to the light guide such that light propagating along said optical path is incident on said boundary at an angle θ, where $$\sin^{-1}\frac{n_e(f)}{n_g(f)} > \theta > \sin^{-1}\frac{n_l(f)}{n_g(f)}$$

over at least a portion of the frequency range which the light source is configured to emit and the light detector is configured to detect, $n_e(f)$ being the refractive index of gas occupying any volume of the cavity not occupied by the liquid.

The gas occupying any volume of the cavity not occupied by the liquid can comprise air.

The liquid store can extend in an elongate direction from a first end to a second end; the light source can be located at the first end; and the light detector can be located at the second end.

The light guide can comprise a plurality of light guide portions; wherein a first light guide portion (4141) of the plurality of light guide portions is optically coupled to the light source; a last light guide portion (4144) of the plurality of light guide portions is optically coupled to the light detector; and each successive light guide portion is optically coupled to the next by a reflecting surface.

There can be at least four reflecting surfaces.

The liquid store can extend in an elongate direction from a first end to a second end; and the light source and the light detector can both be located at the first end.

The light guide can be configured to transmit light transverse to the elongate direction.

The system can further comprise a vaporizer, wherein the light guide is located in a position offset from the vaporizer.

The vaporizer can comprise a heater (3730, 4730) and a fluid transfer element (3720, 4720).

The liquid store can further comprise an external wall in which the light guide is comprised.

The liquid store can further comprise an external wall which at least partially surrounds the light guide.

The liquid store can further comprise an internal wall in which the light guide is comprised.

The light guide can be provided with a channel (4710) configured to permit flow of vapor out of the vaporizer during use of the electronic cigarette.

The system can further comprise a controller (2500) communicably coupled to the light detector and configured to determine, in dependence on a signal received from the light detector: a volume of liquid in the cavity; and/or a refractive signature generated by interaction of light transmitted by the light guide with any liquid in the cavity.

The system can further comprise a memory communicably coupled to the controller. The memory can be local to the controller, communicably coupled by a wired or wireless connection, for example within a liquid cartridge in which the system is comprised or within an electronic cigarette in which the system is comprised. Alternatively the memory could be remote from the controller.

The system can further comprise an orientation detector communicably coupled to the controller, wherein the controller is configured to determine said volume of liquid and/or said refractive signature further in dependence on a signal received from the orientation detector.

The controller determining said volume of liquid and/or said refractive signature further in dependence on a signal received from the orientation detector can comprise the controller incorporating the signal received from the orientation detector in a calculation to determine said volume of liquid and/or said refractive signature. Alternatively or additionally, the controller determining said volume of liquid and/or said refractive signature further in dependence on a signal received from the orientation detector can comprise the controller only determining said volume of liquid and/or said refractive signature if the signal received from the orientation detector indicates that the system's orientation is within a predetermined range.

The orientation detector could comprise the light source, light guide and light detector and be configured to detect orientation by comparing light detector signals corresponding to two or more different optical paths from the light source, through the light guide, to the light detector.

The light guide can comprise two or more liquid traps for liquid contained in the cavity to pool in when the volume of liquid in the cavity is sufficiently high and the cavity is in a suitable orientation, each of said two or more different optical paths comprising reflections from a different set of liquid trap surfaces.

The controller can be communicably coupled to the light source and configured to control the light source to emit light bursts according to a predetermined schedule.

The system can further comprise a user input device, wherein the controller is communicably coupled to both the light source and the user input device and is configured to control the light source to emit light bursts in response to a signal received from the user input device.

The system can further comprise a user output device (2400), wherein the controller is communicably coupled to the user output device and is configured to control the user output device to alert the user in response to determining that: the determined volume of liquid is below a predetermined threshold; and/or the determined refractive signature is outside of a predetermined range.

The system can further comprise a vaporizer, wherein the controller is configured to enable the vaporizer in response to a signal from a user input device, provided that: the determined volume of liquid is above a predetermined threshold; and/or the determined refractive signature is within a predetermined range.

The vaporizer can comprise a heater (3730, 4730). Enabling the vaporizer can comprise causing the heater to switch on.

According to a second aspect there is provided an electronic cigarette comprising the system of the first aspect.

According to a third aspect there is provided a liquid cartridge (2700, 3700, 4700) for an electronic cigarette (2000) comprising the system of the first aspect.

According to a fourth aspect there is provided a method (500) for determining contents of the liquid cartridge the method comprising: receiving (510) a signal from the light detector; and responsive thereto, determining (520), in dependence on the signal received from the light detector: a volume of liquid in the cavity; and/or a refractive signature generated by interaction of light transmitted by the light guide with any liquid in the cavity.

Said volume of liquid and/or said refractive signature can be determined further in dependence on a signal received from an orientation detector.

Said volume of liquid and/or said refractive signature can be determined by comparing light detector signals corresponding to two or more different optical paths from the light source, through the light guide, to the light detector.

The method can further comprise, prior to receiving the signal from the light detector, controlling the light source to emit a light burst.

The method can further comprise: determining (530) that: the determined volume of liquid is below a predetermined threshold; and/or the determined refractive signature is outside of a predetermined range; and responsive thereto, triggering (531) a user alert.

The method can further comprise: receiving (501) a signal from a user input device; determining (530) that: the determined volume of liquid is above a predetermined threshold; and/or the determined refractive signature is within a predetermined range; and in response to both said determination and receiving the signal from the user input device, enabling (532) a vaporizer.

The method can further comprise: writing (534) an indication of the signal from the light detector to a memory;

subsequent to enabling the vaporizer, receiving (501) a further signal from the user input device and a further signal from the light detector; responsive thereto, determining (530) whether the further signal from the light detector matches the indication stored in the memory; and enabling (532) the vaporizer provided that the further signal from the light detector matches the indication stored in the memory.

According to a fifth aspect there is provided a computer readable medium comprising executable instructions which, upon execution by a device, cause the method of the fourth aspect to be performed.

BRIEF DESCRIPTION OF THE FIGURES

Aspects of the present disclosure will now be described by way of example with reference to the accompanying figures. In the figures.

DETAILED DESCRIPTION OF THE FIGURES

Figure 1:
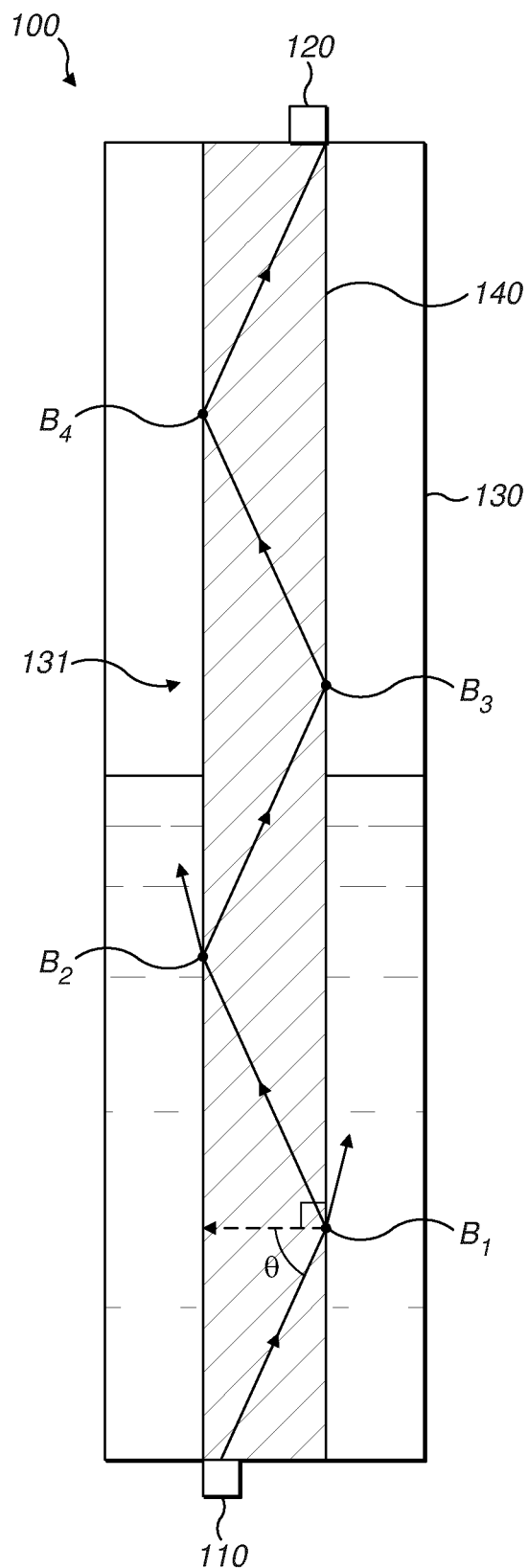
FIG. 1 illustrates the principle of operation of an example liquid detecting system.

The following description is presented to enable any person skilled in the art to make and use the system, and is provided in the context of a particular application. Various modifications to the disclosed embodiments will be readily apparent to those skilled in the art.

The terms "top", "bottom", "side", "front", "back", "forward", "rear" and other terms describing the orientation of features are not intended to be limiting and, where used, are purely included in order to facilitate the description of the relative location of these features in the context of the accompanying drawings. In use, or during storage, the features may be disposed in other orientations.

The present inventors have recognised that the way in which light internally reflects and, under some circumstances, refracts when it encounters a boundary between two transmission media can be used to determine the contents of a liquid store for an electronic cigarette.

When a light beam is transmitted through a first medium towards a boundary with a second medium it may be entirely reflected from the boundary or it may be partially refracted into the second medium and partially reflected back into the first. The proportion of light reflected, the phase shift introduced by the reflection and the polarisation of the reflected light all depend on the refractive indices of the two media and on the angle at which the light beam strikes the boundary, according to the Fresnel equations.

The condition for total internal reflection to occur is that the angle of incidence on the boundary, with respect to the normal to the boundary at the point of incidence, is larger than the critical angle $\theta_c$ given by Snell's law:

$$\theta_c = \sin^{-1}\frac{n_2}{n_1} \tag{1}$$

where $n_1$ and $n_2$ are the refractive indices of the first and second media respectively.

According to the present disclosure, light reflected from a boundary between a light guide and an internal cavity of a liquid store is detected in order to determine the presence/absence/level of a liquid in the liquid store and/or its identity. A proposed liquid detecting system is arranged such that the properties of light emitted by a light source are known, the angle of incidence of a light beam emitted by that light source on said boundary is known and the refractive index of the light guide is known. In this way the detected light can indicate the refractive index of the medium filling the cavity at the point of incidence of the light beam on the boundary. The system can therefore be arranged such that the detected light will differ depending on whether the liquid level is above or below the point of incidence of the light beam on the boundary, and on the composition of the liquid. The light guide is arranged such that, in at least one orientation, any liquid contained in the cavity will pool against said boundary.

The system may be arranged such that, when held in an orientation typical for use, the light source directs light along an optical path to the light detector which incorporates total internal reflection at the boundary when the liquid level is above a predetermined minimum fill level but not when the liquid level is below that predetermined minimum fill level, or vice-versa. For this to occur, the refractive indices of the light guide ($n_g$), liquid ($n_l$) and the gas/vapor mixture occupying the volume of the cavity not occupied by the liquid, which will typically be air, ($n_a$) must obey either:

$$n_a < n_g < n_l \tag{2}$$

or $$n_a > n_g > n_l \tag{3}$$

The refractive indices are frequency-dependent, so for either of conditions (2) or (3) to occur this inequality must be true over at least a portion of a frequency range which the light source is configured to emit and the light detector is configured to detect. For example, the center frequencies of the light source and light detector could be configured to be substantially identical, and the materials chosen for the light guide and the liquid could be chosen to have refractive indices satisfying one of inequalities (2) and (3) at that center frequency.

The principle of operation is illustrated schematically in FIG. 1, which shows an example system 100 comprising a light source 110, a light detector 120, a liquid store 130 comprising an internal cavity 131 for holding liquid, which is shown partially full, and a light guide 140.

A light beam emitted by the light source 110 follows an optical path through the light guide 140 to the light detector 120 via internal reflection at points $B_1$, $B_2$, $B_3$ and $B_4$ in that order. In this example the light guide 140 is a straight rod so the angle of incidence, $\theta$, at point $B_1$ is also the angle of incidence at points $B_2$, $B_3$ and $B_4$. (The angle of incidence is the angle between the light ray and the normal to the boundary at the point of incidence.) In this example inequality (2) is satisfied so at points $B_1$ and $B_2$ (which are below the fill level) some of the light is reflected and some refracted out into the liquid, while at points $B_3$ and $B_4$ (which are above the fill level) the light is totally internally reflected.

In this example, it is possible to determine from the light detected by light detector 120 that the fill level is somewhere between points $B_2$ and $B_3$.

Figure 2:
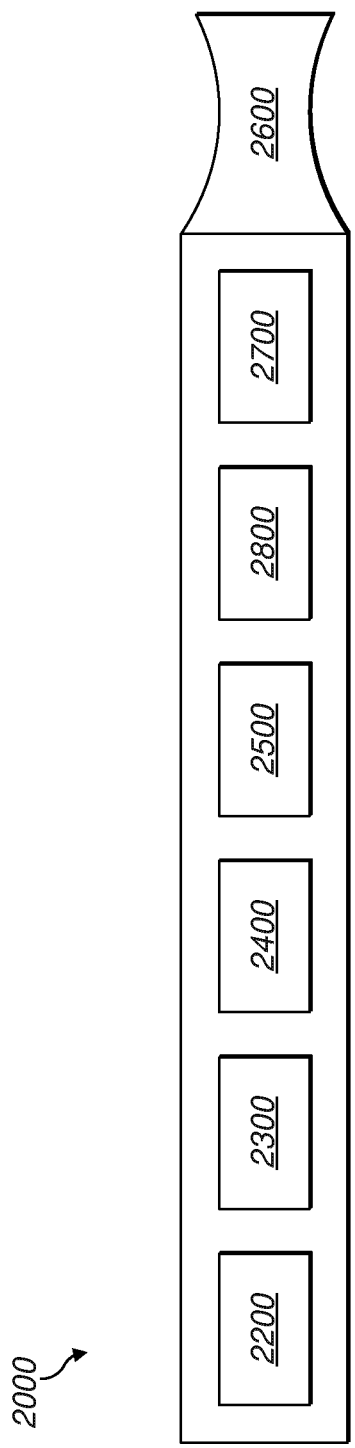
FIG. 2 schematically illustrates an example electronic cigarette.

FIG. 2 schematically illustrates an example electronic cigarette 2000 which a liquid detecting system such as the system 100 of FIG. 1 may be used in. The electronic cigarette 2000 comprises a power supply 2200 such as a battery, one or more user input devices 2300, one or more user output devices 2400 and a controller or processor 2500. The controller 2500 receives signals from the one or more user input devices 2300 and controls the one or more user output devices 2400 in response thereto. The electronic cigarette 2000 further comprises a mouthpiece 2600 and a cartridge 2700 comprising a liquid store, a heater and a fluid transfer element. (The liquid store could alternatively be provided separately from a vaporizer comprising a heater and a fluid transfer element.)

The power supply 2200 supplies power to the one or more user input devices 2300, one or more user output devices 2400, controller or processor 2500 and cartridge 2700 as required.

The electronic cigarette 2000 further comprises a memory module 2800 for accessing a memory. That memory can store instructions for the controller 2500 to execute and/or parameters for the controller 2500 to use in calculations (such as predetermined threshold values) and/or can be used to store data collected by the light detector. The module 2800 can comprise one or more local memories and/or a transceiver for communicating with one or more remote memories, for example by Bluetooth™, WiFi, near-field communication (NFC) or over a wired connection.

In the same way that the memory module 2800 can provide for certain functions to be performed locally to the electronic cigarette 2000 or remotely, processing described as being performed by the controller 2500 could also be performed locally or remotely. For example some or all processing tasks could be performed by a smartphone or other user device executing electronic cigarette companion software such as a companion app.

The cartridge 2700 may be switched on in response to user input through a user input device 2300. For example user input device 2300 could be a button. Alternatively user input device 2300 could be a flow sensor configured to detect when air is being drawn into the electronic cigarette 2000 from an air inlet through the cartridge 2700 and out of the mouthpiece 2600.

Figure 3A:
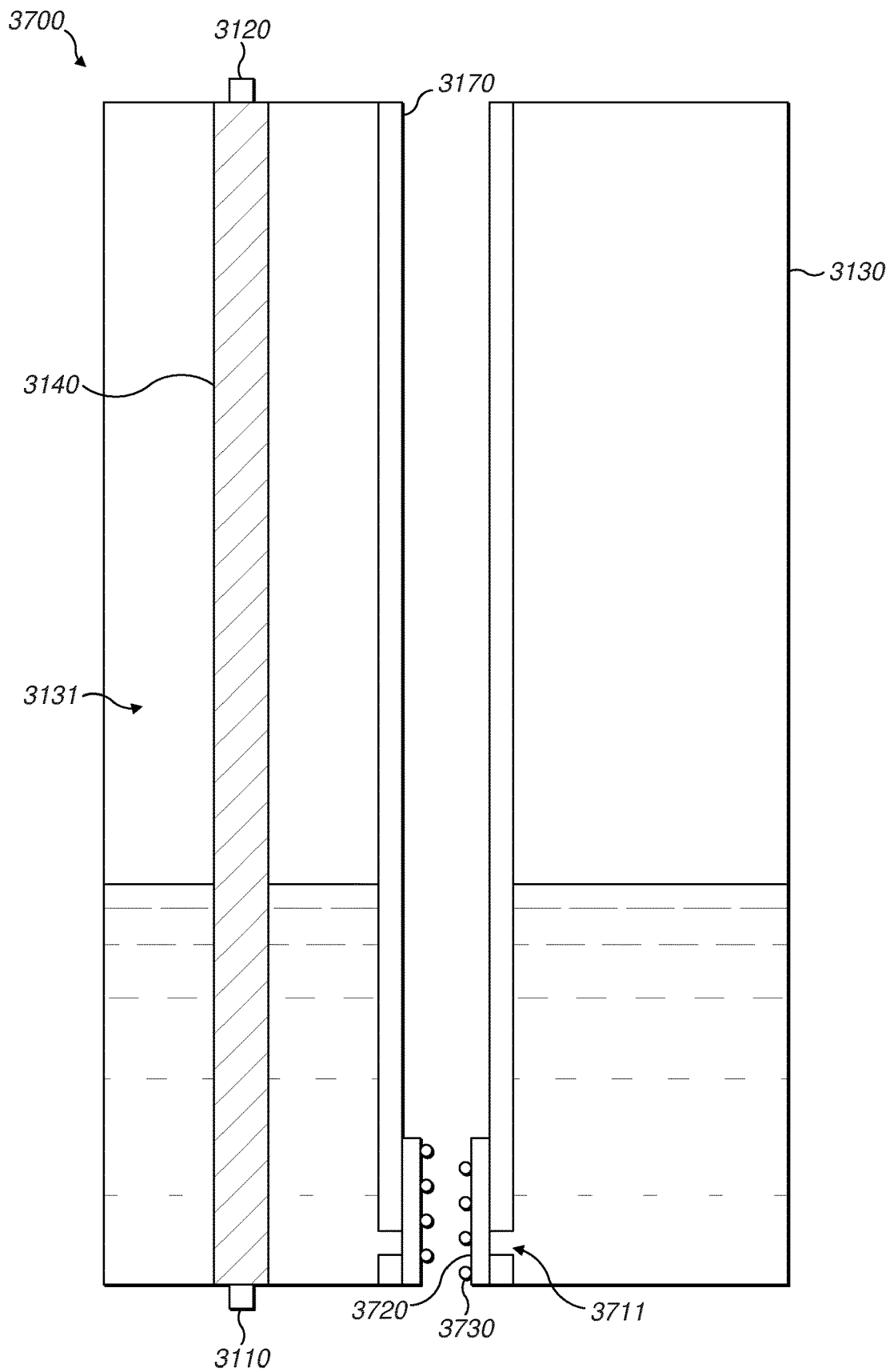
FIG. 3A schematically illustrates an example cartridge.

FIG. 3A schematically illustrates an example cartridge 3700, which could be used as the cartridge 2700 of the electronic cigarette 2000 of FIG. 2. The cartridge 3700 comprises a vapor flow tube 3710, within which is located a fluid transfer element 3720 and a heater 3730. The vapor flow tube 3710 is within a liquid store 3130 having a cavity 3131 for containing liquid. The cavity 3131 is shown partially full. The vapor flow tube 3710 comprises one or more liquid inlets 3711, typically towards the end of the cartridge 3700 which is generally lowest in use. The one or more liquid inlets 3711 allow liquid from the cavity 3131 to soak into the fluid transfer element 3720. That liquid in the fluid transfer element 3720 is vaporized when the heater 3730 is switched on. As drawn, the vaporizer is a vertical fluid transfer element vaporizer. A horizontal fluid transfer element could alternatively be used, for example with the fluid transfer element extending across the vapor flow tube from one liquid inlet to another and the heater coiling around the fluid transfer element.

The cartridge 3700 further comprises a light guide 3140, light source 3110 and light detector 3120 which operate in a similar way to the corresponding elements of FIG. 1. The light guide 3140 can be located such that the cavity 3131 surrounds it. Alternatively the light guide 3140 can form part of, or extend out of, a side wall of the liquid store 3130.

In an alternative example, the vapor flow tube itself could be the light guide.

Figure 3B:
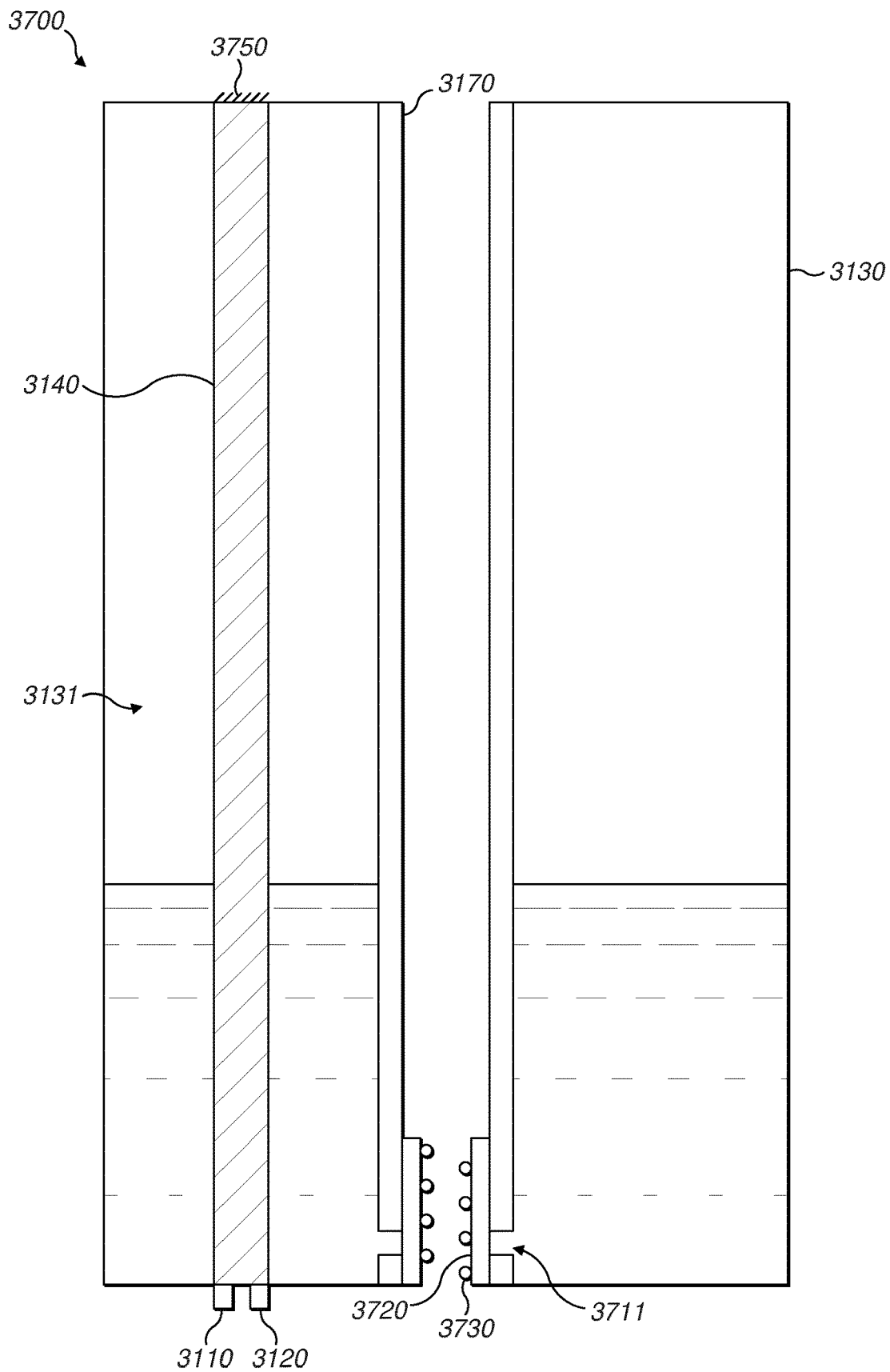
FIG. 3B schematically illustrates an alternative example cartridge.

A further alternative example is illustrated in FIG. 3B, wherein the reference numerals shared with FIG. 3A designate corresponding components. In this example the light source 3110 and light detector 3120 are both located at the same end of the cartridge 3700. As shown they are located at the same end as the vaporizer, though they could alternatively be located at the opposite end. Since the light source 3110 and light detector 3120 are located at the same end of the light guide 3140, the optical path followed by the light beam from the light source 3110 to the light detector 3120 must comprise a reflection at the other end of the cartridge 3700. This is accomplished using a mirror 3750, which could be a separate component or could be an end face of the light guide 3140. Keeping the light source 3110 and light detector 3120 close together can simplify the electrical connections, especially where the cartridge 3700 is replaceable and the battery or other power supply 2200 is located separately as a permanent component of the electronic cigarette 2000.

Figure 4A:
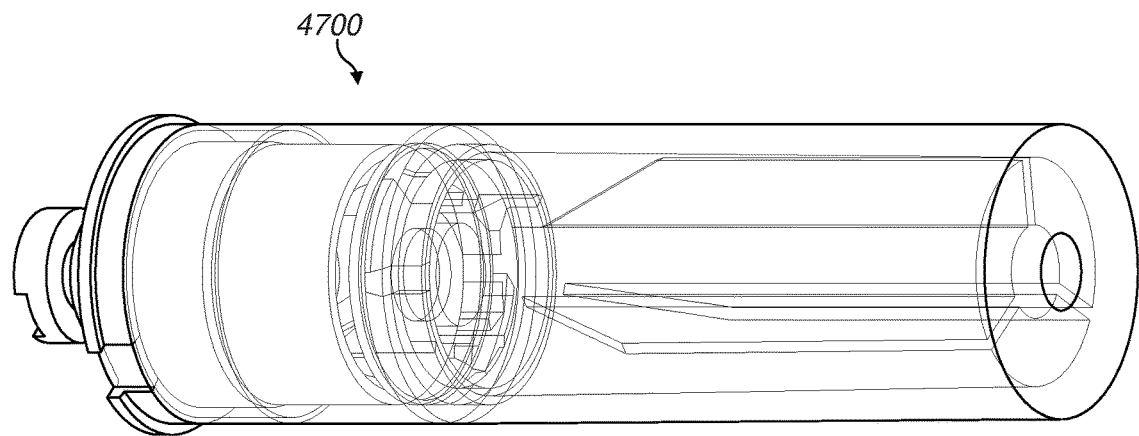
FIG. 4A illustrates an alternative example cartridge fully assembled.
Figure 4B:
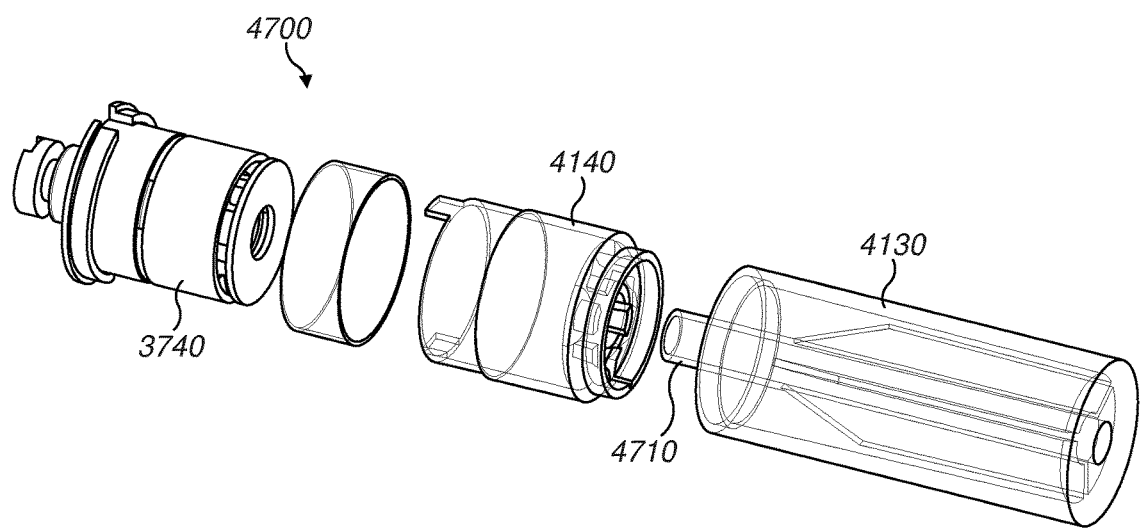
FIG. 4B shows some of the components of FIG. 4A in exploded form.
Figure 4C:
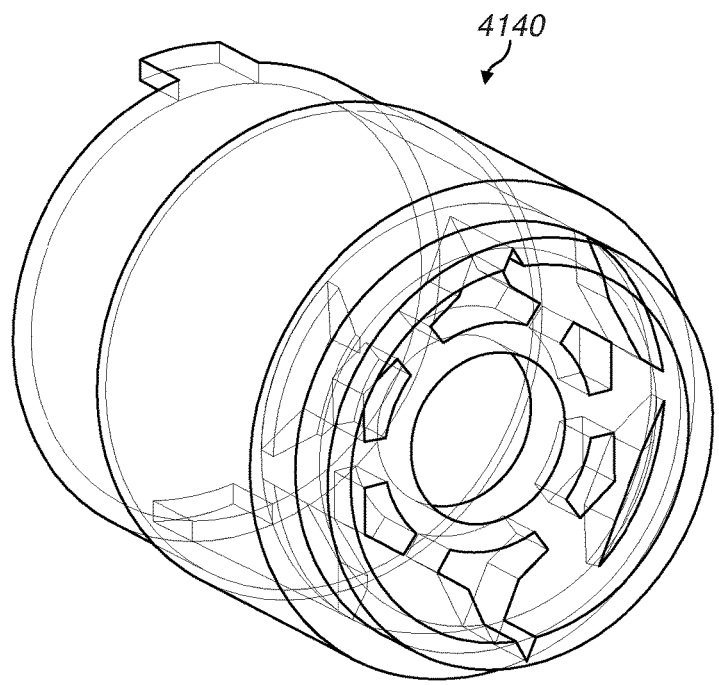
FIG. 4C shows a light guide of FIGS. 4A and 4B in more detail.

FIGS. 4A to 4E illustrate an alternative example cartridge 4700, which could be used as the cartridge 2700 of the electronic cigarette 2000 of FIG. 2. FIG. 4A shows the cartridge 4700 fully assembled, while FIG. 4B shows some of its components in exploded form. The cartridge 4700 comprises a liquid store 4130 which surrounds an axial vapor flow tube 4710. These fit inside a light guide 4140 which fits over a vaporizer 3740. FIG. 4C shows the light guide 4140 in more detail.

Figure 4D:
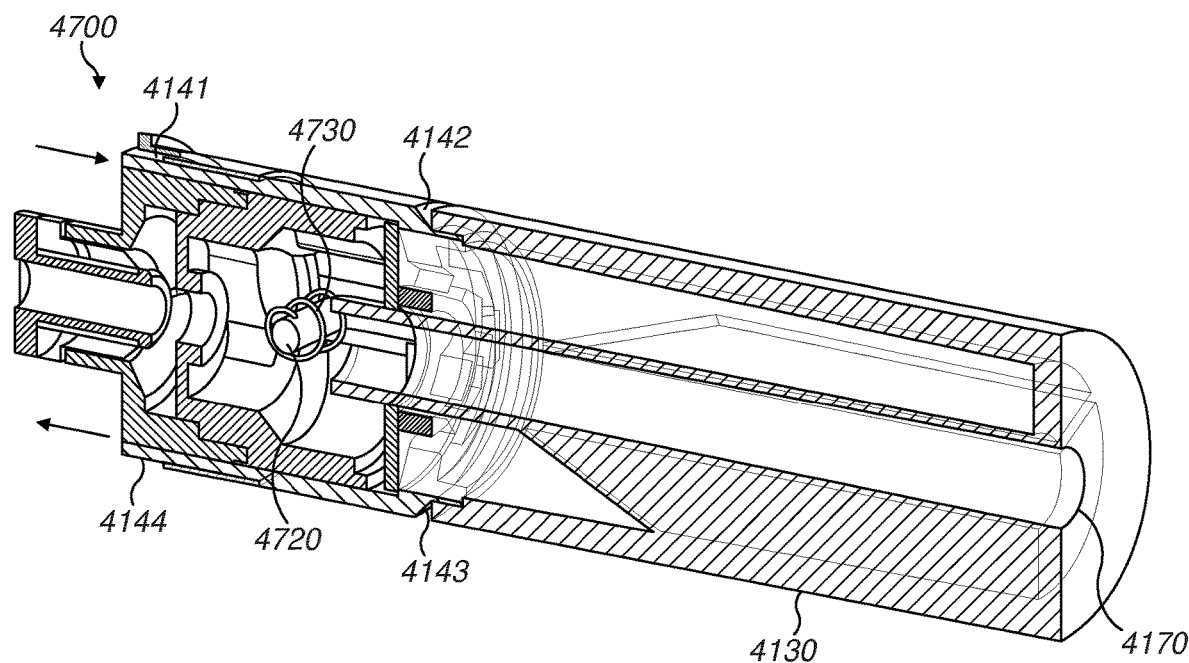
FIG. 4D shows an axial cross section through the cartridge of FIGS. 4A to 4C.
Figure 4E:
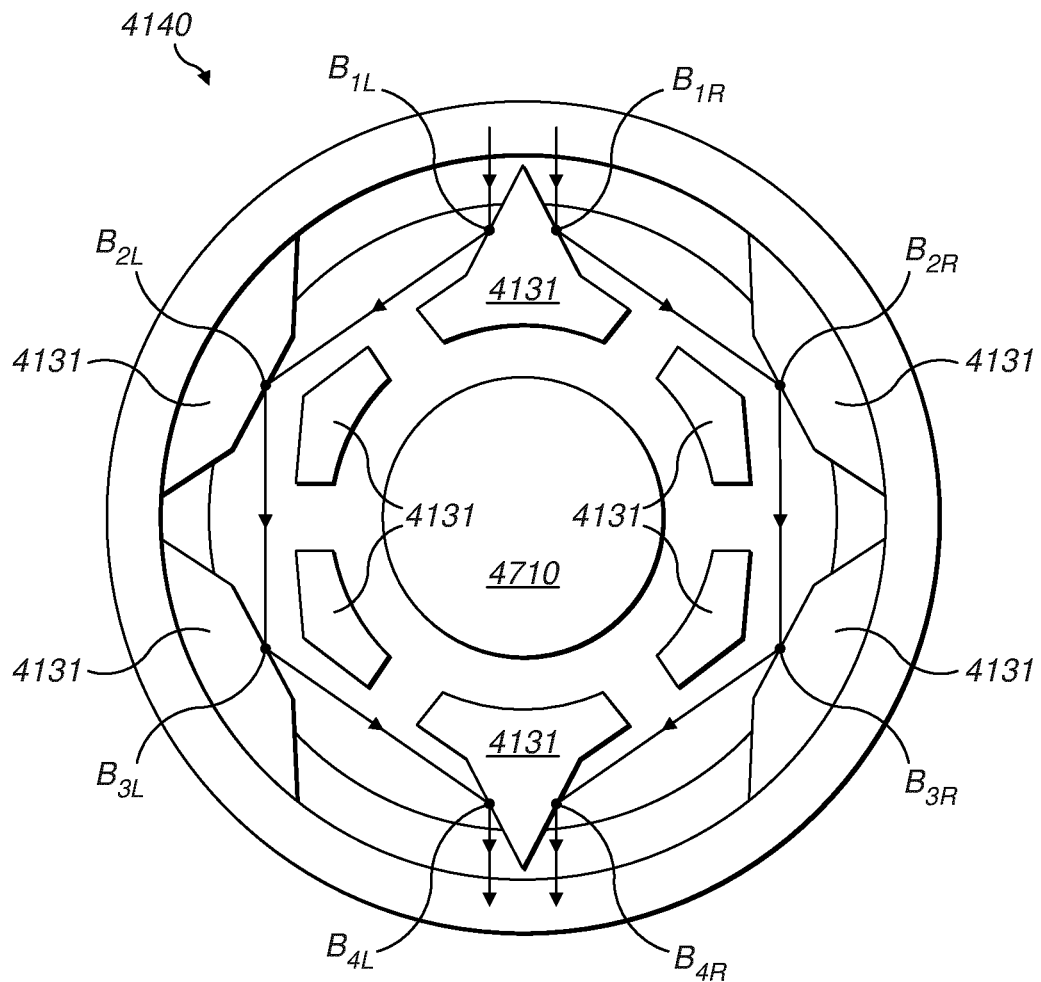
FIG. 4E shows a radial cross section through the cartridge of FIGS. 4A to 4D.

Operation of the liquid detection system of the cartridge 4700 is illustrated by FIGS. 4D and 4E which respectively show an axial cross section through the cartridge 4700 and a radial cross section through the cartridge 4700 illustrating the shape of the light guide 4140. The vapor flow tube 4710 runs through the center of the light guide 4140. In a region in which it engages with the light guide 4140 the liquid store 4130 is formed into a number of hollow prongs which extend through the light guide 4140, forming liquid traps in which any liquid contained in the cavity 4131 of the liquid store can pool, depending on the fill level and orientation of the liquid store 4130.

As shown in FIG. 4D, light from a light source (not shown) enters the light guide 410 in a substantially longitudinal direction with respect to the cartridge's axis through a light pipe 4141. The light then reflects off a chamfer 4142, which is angled at approximately 45°, so that the direction of the optical path is changed to substantially transverse with respect to the cartridge's axis.

FIG. 4E shows the next stage of the light beam's journey, where it is directed by reflections at boundaries with portions of the cavity 4131 of the liquid store 4130 which extend into the light guide 4140. The light beam is split by the first portion of the cavity 4131 which it encounters, with a first optical path comprising a reflection at point $B_{1L}$ followed by further reflections at points $B_{2L}$, $B_{3L}$ and $B_{4L}$ in that order, and a second optical path comprising a reflection at point $B_{1R}$ followed by further reflections at points $B_{2R}$, $B_{3R}$ and $B_{4R}$ in that order.

The two optical paths illustrated in FIG. 4E then both encounter a further chamfer 4143 which, as shown in FIG. 4D, performs the reverse function to the chamfer 4142, namely changing the direction of the light beam's path from substantially transverse to the cartridge's axis to substantially longitudinal with respect to the cartridge's axis. The light beam then exits the light guide 4140 through a longitudinal light pipe 4144, similar to light pipe 4141, which leads to a light detector (not shown).

Since the example light guide of FIG. 4 splits the optical path into portions around both halves of the liquid store's circumference, liquid can be detected even if there is only a small amount remaining and the cartridge is not perfectly oriented. If the light detector is configured so as to distinguish between rays which followed the left hand optical path and rays which followed the right hand optical path then the orientation of the cartridge 4700 can also be determined from the light detector readings.

An alternative or additional orientation detector could be provided in any of the example systems described above, for example one or more gyroscopes and/or accelerometers could be provided for orientation detection.

Any orientation detector provided in the electronic cigarette 2000 could provide readings to the controller 2500, wherein the controller is configured to determine the volume of liquid in the liquid store and/or a refractive signature of the liquid store's contents in dependence on a signal received from the orientation detector. For example, an algorithm used to make these determinations could incorporate the reading from the orientation detector. Alternatively or additionally, the orientation detector signaling that the electronic cigarette 2000 is substantially in a predetermined "correct" orientation may be a prerequisite for making such determinations. For example, if the orientation detection does not rely on the optical components, the light source may only be permitted to switch on if the orientation is determined to be correct.

The light source could be configured to pulse periodically or according to some other predetermined schedule so as to continuously monitor the contents of the liquid store. Alternatively it could be configured to pulse only when a user input device indicates that use of the electronic cigarette is required.

In any of the examples described above, one or more user output devices 2400 could be used to alert the user of the result of any determination made by the liquid detection system. For example a buzzer could sound or a red indicator light could flash following a determination of low liquid level and/or unauthorized liquid type. Alternatively or additionally an indicator light could be used to inform the user that the liquid level is sufficiently high and/or that the liquid is authorized. A screen, such as a liquid crystal display (LCD) could be used to convey such information using text or symbols, e.g. a fill level indicator similar to the battery charge indicators familiar to users from mobile devices such as mobile phones. If the electronic cigarette 2000 is a connected device then determinations made by the liquid detecting system could be provided via other user devices, such as through a companion smartphone app.

The electronic cigarette 2000 may be configured to only permit use of the electronic cigarette if a positive determination can be made by the liquid detection system that the liquid fill level is sufficiently high and/or that the liquid is authorized. For example, the electronic cigarette 2000 may only be enabled in response to such a positive determination.

Light sources and light detectors can be chosen as appropriate in each example described above. The light source can for example be a light emitting diode (LED) or a laser. The light detector can for example be a photodiode or a charge-coupled device (CCD).

The light guide can for example be formed of a transparent or translucent material, for example glass or a plastic such as polycarbonate. It could for example be polyethylene, which has a refractive index of 1.458 or poly(methyl methacrylate) (PMMA), which has a refractive index of 1.4906. Any surfaces of the light guide contacting the liquid should be formed of food grade approved substances so as not to contaminate the liquid. The light guide could be solid, or could for example be a liquid or gas-filled tube. In the latter case, the thickness of the tube walls and the liquid or gas filling it can be chosen to provide a suitable refractive index.

The refractive index, $n_l(f)$ of the liquid can for example be between 1.40 and 1.50 as conventionally measured at the yellow doublet D-line of sodium, with a wavelength of 589 nm. For example, it may be propylene glycol (PG), which has a refractive index of 1.4399, or vegetable glycerine (VG), which has a refractive index of 1.4731, or a mixture of these.

The liquid store could be part of a disposable cartridge, or could be configured as a permanent refillable component of a mouthpiece portion. Hence, the enabling system can be applied when adding liquid to a permanent liquid store as required or when replacing a disposable liquid cartridge. If the liquid is provided in replaceable cartridges then the cartridges may comprise other components described above, such as the vaporizer, liquid detection system, or elements thereof.

Since liquid level changes in the liquid store during use, the light signal will be different for a new cartridge than for a used cartridge. Therefore, a measurement of the light signal may be performed each time the electronic cigarette is turned off. This measurement can be referred to as a variable authentication value and can for example be stored in a re-writable volatile memory. The electronic cigarette thus saves an authentication signature in its memory after use. The liquid cartridge or the liquid in the refillable liquid store can therefore be authenticated with this signature the next time the electronic cigarette is used.

Figure 5:
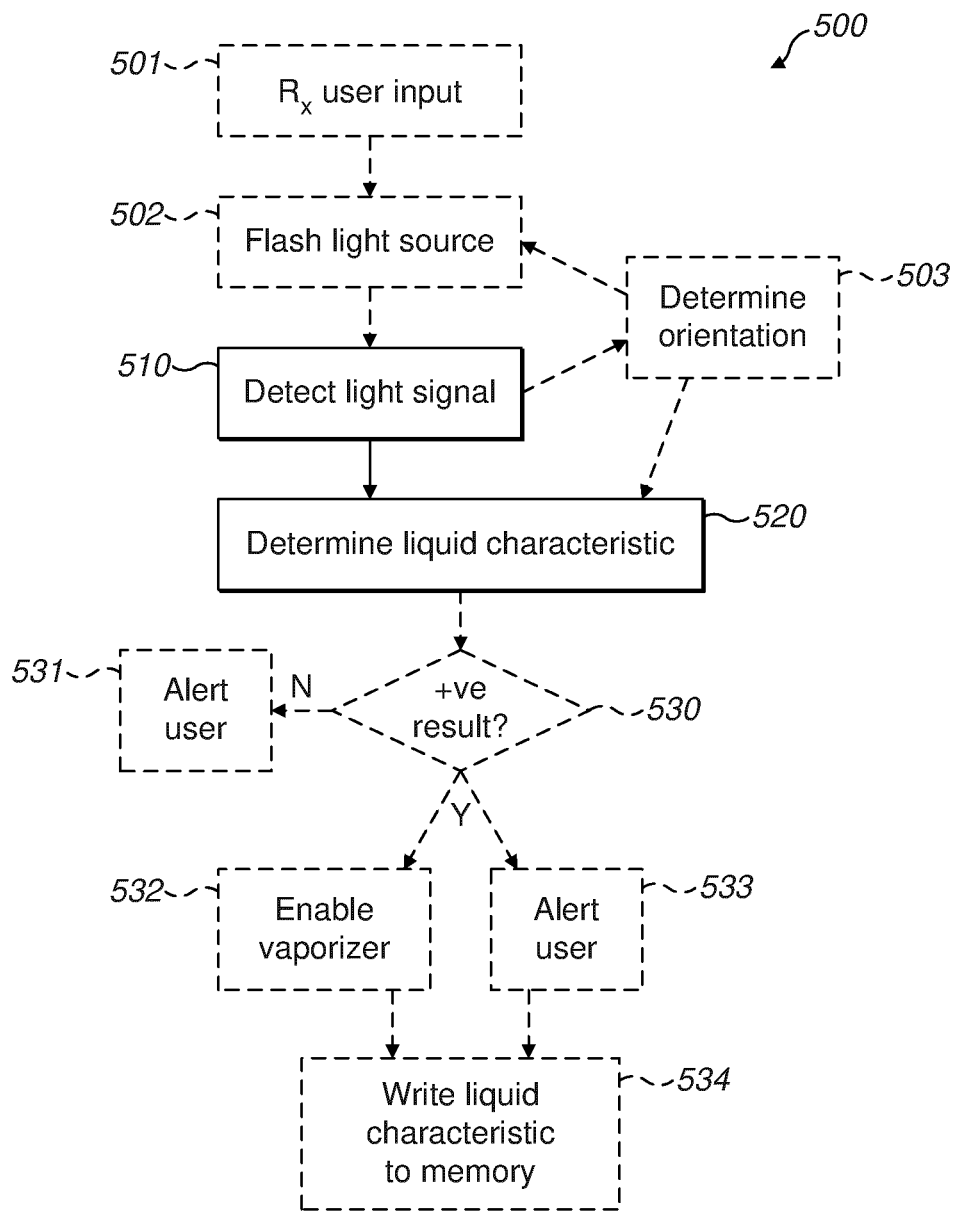
FIG. 5 is a flowchart illustrating an example method for use of a liquid detection system.

FIG. 5 is a flowchart illustrating an example method 500 for use of a liquid detection system such as the system 100 described above. At step 510 a light signal is detected. In response to this, at step 520 a liquid characteristic is detected, such as volume (binary presence/absence or quantitative fill level) or refractive signature of liquid in the liquid store cavity.

Step 510 may optionally be preceded by certain steps. For example, user input may be received at step 501 from a user input device. In response to this the light source could be enabled at step 502, for example by being briefly pulsed or flashed. Alternatively step 502 could be enacted according to a predetermined schedule as described above.

Step 503, to determine the orientation of the liquid store, can also be incorporated in several ways. If the orientation detection relies on the optical components then step 503 may follow detection of the light signal at step 510. Alternatively, if the orientation is determined in some other way then the light source could be enabled at step 502 in response to the orientation detection at step 503. In some examples the liquid characteristic determination at step 520 may involve a calculation incorporating the orientation determination made at step 503.

Step 520 may optionally be followed by certain further steps. For example, the result of the liquid characteristic determination can be queried relative to some predetermined criteria at query 530. If the result is determined to be negative, for example because the result indicates insufficient liquid level for use, or that an unauthorized liquid is present, the user can be alerted at step 531 by means of a user output device. If the result is determined to be positive on the other hand, the vaporizer may be enabled at step 532 and/or the user may be alerted at step 533.

The liquid characteristic may additionally be written to memory at step 534. If so, query 530 may be determined with respect to the stored result. For example, if a liquid characteristic determined at a later time is found to match one which was recorded as positive previously then the result can be determined to be positive again without requiring any other calculation.

Other embodiments will be apparent to those skilled in the art from consideration of the specification and practice of the embodiments disclosed herein. It is intended that the specification and examples be considered as exemplary only.

In addition, where this application has listed the steps of a method or procedure in a specific order, it could be possible, or even expedient in certain circumstances, to change the order in which some steps are performed, and it is intended that the particular steps of the method or procedure claims set forth herein not be construed as being order-specific unless such order specificity is expressly stated in the claim. That is, the operations/steps may be performed in any order, unless otherwise specified, and embodiments may include additional or fewer operations/steps than those disclosed herein. It is further contemplated that executing or performing a particular operation/step before, contemporaneously with, or after another operation is in accordance with the described embodiments.

The methods described herein may be encoded as executable instructions embodied in a computer readable medium, including, without limitation, non-transitory computer-readable storage, a storage device, and/or a memory device. Such instructions, when executed by a processor/controller (or one or more computers, processors, controllers and/or other devices) cause the processor/controller (the one or more computers, processors, controllers and/or other devices) to perform at least a portion of the methods described herein. A non-transitory computer-readable storage medium includes, but is not limited to, volatile memory, non-volatile memory, magnetic and optical storage devices such as disk drives, magnetic tape, compact discs (CDs), digital versatile discs (DVDs), or other media that are capable of storing code and/or data.

Where a processor or controller is referred to herein, this is to be understood to refer to a single processor or controller or multiple processors or controllers operably connected to one another. Similarly, where a memory is referred to herein, this is to be understood to refer to a single memory or multiple memories operably connected to one another.

The methods and processes can also be partially or fully embodied in hardware modules or apparatuses or firmware, so that when the hardware modules or apparatuses are activated, they perform the associated methods and processes. The methods and processes can be embodied using a combination of code, data, and hardware modules or apparatuses.

Examples of processing systems, environments, and/or configurations that may be suitable for use with the embodiments described herein include, but are not limited to, embedded computer devices, personal computers, server computers (specific or cloud (virtual) servers), hand-held or laptop devices, multiprocessor systems, microprocessor-based systems, set top boxes, programmable consumer electronics, mobile telephones, network personal computers (PCs), minicomputers, mainframe computers, distributed computing environments that include any of the above systems or devices, and the like. Hardware modules or apparatuses described in this disclosure include, but are not limited to, application-specific integrated circuits (ASICs), field-programmable gate arrays (FPGAs), dedicated or shared processors, and/or other hardware modules or apparatuses.

Receivers and transmitters as described herein may be standalone or may be comprised in transceivers. A communication link as described herein comprises at least one transmitter capable of transmitting data to at least one receiver over one or more wired or wireless communication channels. Such a communication link can optionally further comprise one or more relaying transceivers.

User input devices can include, without limitation, microphones, buttons, keypads, touchscreens, touchpads, trackballs, joysticks and mice. User output devices can include, without limitation, speakers, buzzers, display screens, projectors, indicator lights, haptic feedback devices and refreshable braille displays. User interface devices can comprise one or more user input devices, one or more user output devices, or both.

The invention claimed is:

1. A liquid detecting system for an electronic cigarette, the system comprising:
   a light source;
   a light detector;
   a liquid store comprising an internal cavity for holding liquid;
   a light guide optically coupled to both the light source and the light detector such that light emitted from the light source propagates towards the light detector along an optical path comprising an internal reflection within the light guide at a boundary with the cavity, such that light received by the light detector along said optical path varies depending on contents of the cavity; and
   a vaporizer, wherein the light guide is located in a position offset from the vaporizer and wherein the light guide is provided with a channel configured to permit flow of vapor out of the vaporizer during use of the electronic cigarette.

2. The system of claim 1, wherein the cavity comprises liquid having a refractive index, $n_l(f)$, which is higher than a refractive index, $n_g(f)$, of the light guide over at least a portion of a frequency, f, range which the light source is configured to emit and the light detector is configured to detect.

3. The system of claim 2, wherein the light source is located with respect to the light guide such that light propagating along said optical path is incident on said boundary at an angle θ, where $$\sin^{-1}\frac{n_e(f)}{n_g(f)} > \theta > \sin^{-1}\frac{n_l(f)}{n_g(f)}$$

over at least a portion of the frequency range which the light source is configured to emit and the light detector is configured to detect, $n_e(f)$ being a refractive index of gas occupying any volume of the cavity not occupied by the liquid.

4. The system of claim 1, wherein:
the liquid store extends in an elongate direction from a first end thereof to a second end thereof;
the light source is located at the first end; and
the light detector is located at the second end.

5. The system of claim 1, wherein:
the liquid store extends in an elongate direction from a first end thereof to a second end thereof; and
the light source and the light detector are both located at the first end.

6. The system of claim 5, wherein the light guide is configured to transmit light transverse to the elongate direction.

7. The system of claim 1, wherein:
the light guide comprises a plurality of light guide portions;
a first light guide portion of the plurality of light guide portions is optically coupled to the light source;
a last light guide portion of the plurality of light guide portions is optically coupled to the light detector; and
each successive light guide portion of the plurality of light guide portions is optically coupled to the next light guide portion of the plurality of light guide portions by a reflecting surface.

8. The system of claim 1, further comprising a controller communicably coupled to the light detector and configured to determine, in dependence on a signal received from the light detector:

a volume of liquid in the cavity; and/or
a refractive signature generated by interaction of light transmitted by the light guide with any liquid in the cavity.

9. The system of claim 8, further comprising an orientation detector communicably coupled to the controller, wherein the controller is configured to determine said volume of liquid and/or said refractive signature further in dependence on a signal received from the orientation detector.

10. The system of claim 8, further comprising a user output device, wherein the controller is communicably coupled to the user output device and is configured to control the user output device to alert the user in response to determining that:
the determined volume of liquid is below a predetermined threshold; and/or
the determined refractive signature is outside of a predetermined range.

11. The system of claim 8, wherein the controller is configured to enable the vaporizer in response to a signal from a user input device, provided that:
the determined volume of liquid is above a predetermined threshold; and/or
the determined refractive signature is within a predetermined range.

12. A liquid cartridge for an electronic cigarette, the liquid cartridge comprising the system of claim 1.

* * * * *